(12) United States Patent
Colson et al.

(10) Patent No.: US 6,414,180 B1
(45) Date of Patent: *Jul. 2, 2002

(54) SYNTHESIS OF CHIRAL β-AMINO ACIDS

(75) Inventors: Pierre-Jean Colson; Alok K. Awasthi, both of Skokie, IL (US); Srinivasan R. Nagarajan, Chesterfield, MO (US)

(73) Assignee: G. D. Searle, Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/260,686

(22) Filed: Mar. 2, 1999

Related U.S. Application Data

(60) Provisional application No. 60/076,710, filed on Mar. 4, 1998.

(51) Int. Cl.$^7$ ............................................. C07C 229/00
(52) U.S. Cl. ........................... 560/37; 560/45; 562/442; 562/444
(58) Field of Search ............................. 560/19, 37, 45, 560/433, 442, 443, 444

(56) References Cited

U.S. PATENT DOCUMENTS

| | | | | |
|---|---|---|---|---|
| 3,740,439 A | * | 6/1973 | Eichenberger | 514/567 |
| 3,904,681 A | * | 9/1975 | Eichenberger | 568/446 |
| 5,840,961 A | | 11/1998 | Behling et al. | |

FOREIGN PATENT DOCUMENTS

| | | |
|---|---|---|
| WO | WO97/8145 | 3/1997 |
| WO | WO 98/02410 | 1/1998 |

OTHER PUBLICATIONS

CA:83:178502 abs of Arch Phrm (Weinheim Ger) 308 (5) pp. 339–346, 1975.*
Beilstein BRN 3332265 abs of Zh Obshch Khim by Suworow 28 pp. 1371–1372, 1958.*
CA:126:264011 abs of WO9708145, Mar. 1997.*
Aldrich Chemical Catalogue pp 925, 1996.*
Mokhallalati et al., "Lead Tetraacetate Cleavage of Chiral Phenylglycinol Derived Secondary Amines Without Racemization," Synthetic Communications, 10th ed., vol. 23 (No. 14), pp. 2055–2064, (Jan. 6, 1993).
Mokhallalati et al., "An Efficient Enantiomeric Three Step Synthesis of beta–Amino Acids (Esters)," Tetrahedron Letters, vol. 34 (No. 1), pp. 47–50, (Jan. 6, 1993).
Suvorov et al., "Thyroid Gland Hormones and Their Analogs," ZH. Obshzh. Khim. (English Edition), pp. 1430–1432, (Jan. 6, 1958).

* cited by examiner

*Primary Examiner*—Jean F. Vollano
(74) *Attorney, Agent, or Firm*—Cynthia S. Kovacevic; Alan L. Scivner; Rachel A. Polster

(57) ABSTRACT

The invention herein is directed to a process for the preparation of chiral β-amino acids and esters of the formula

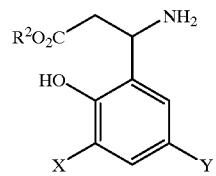

wherein X and Y are the same or different halo groups, $R^2$ is H or lower alkyl and isomers and pharmaceutically acceptable salts thereof.

10 Claims, No Drawings

SYNTHESIS OF CHIRAL β-AMINO ACIDS

The present application claims priority under 35 USC §119(e) of U.S. provisional patent application Serial No. 60/076,710 filed Mar. 4, 1998.

BACKGROUND OF THE INVENTION

The present invention relates to a process for the preparation of chiral β-amino acids and esters of the formula

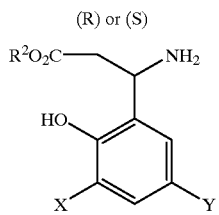

wherein X and Y are the same or different halo group, $R^2$ is H or lower alkyl; which process comprises reacting a 3,5-dihalosalicylaldehyde of the formula

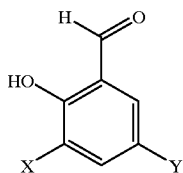

with MEMCl or BnBr (Bn=benzyl) to obtain a protected 3,5-dihalosalicylaldehyde of the formula

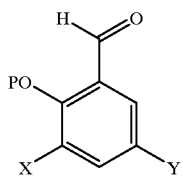

wherein P is Bn or MEM; treating the protected 3,5-dihalosalicylaldehyde with (R) or (S) phenylglycinol in tetrahydrofuran (THF) or toluene to produce an iminoalcohol of the formula

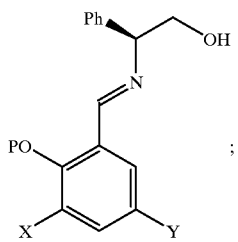

reacting said imino alcohol with $BrZnCH_2CO_2$-t-Bu in N-methylpyrrolidinone (NMP), dimethylsulfoxide (DMSO) or THF to produce an amino alcohol of the formula

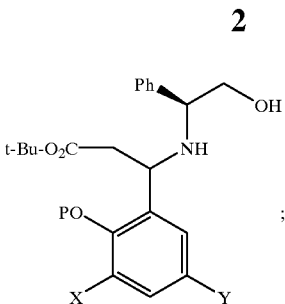

reacting the amino alcohol with lead tetracetate $(Pb(OAc)_4)$ to form an imine of the formula

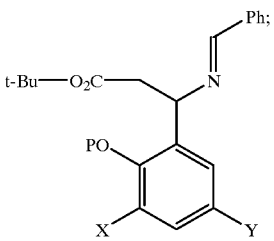

transesterifying, deprotecting, and hydrolyzing said imine in a one pot process to isolate a product of the formula

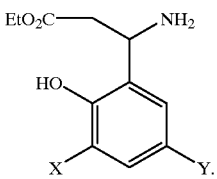

The reaction provides for the preparation of (R) or (S) isomers with enantiomeric excess (ee)>99%.

U.S. Ser. No. 08/890,907 discloses the following process for preparing β-amino acid esters.

Scheme A

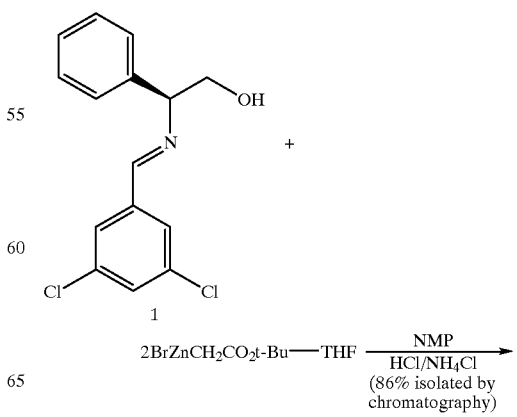

-continued

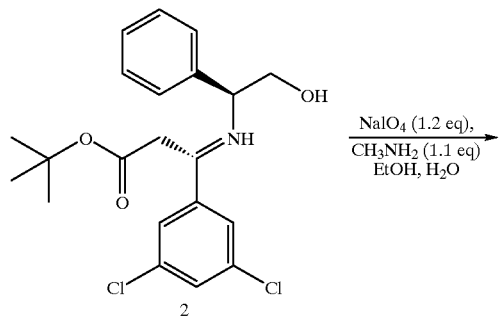

2

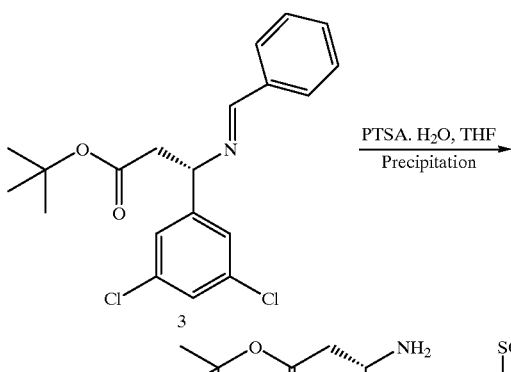

3

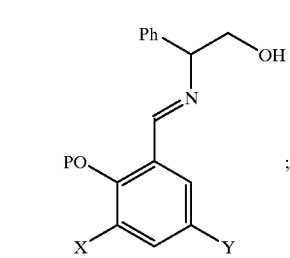

4

Briefly in Scheme A, the chiral imine 1 derived from 3,5-dichlorobenzaldehyde and (S)-phenylglycinol is reacted with 2 equivalents of the Reformatsky reagent (BrZnCH₂CO₂tBu.THF) in NMP at −10° C. to afford the corresponding amino alcohol product 2 as one enantiomer (ee>96%). The amino alcohol 2 was then oxidatively cleaved with sodium periodate in ethanol in the presence of methyl amine to afford the corresponding phenyl imine 3. The β-amino ester 4 was then isolated as a PTSA salt from THF and heptane with an overall yield of 63%.

The chiral β-amino acids and esters produced by the process of the present invention are useful in preparing pharmaceutical agents known as $\alpha_v\beta_3$ integrin antagonists disclosed in WO97/08174. It is therefore desirable to provide a process for the preparation of said amino acids and esters which is amenable to scale-up, and which employs raw materials which are readily available, resulting in high yield and a high level of optical purity which doesn't require any chromatography and/or separation of diastereoisomers.

SUMMARY OF THE INVENTION

The present invention relates to a process for the preparation of chiral β-amino acids and esters of the formula

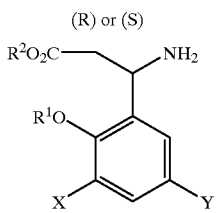

wherein X and Y are the same or different halo group, $R^1$ is H or methoxyethoxymethyl (MEM) and $R^2$ is H or lower alkyl; which process comprises reacting a 3,5-dihalosalicylaldehyde of the formula

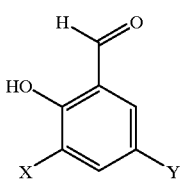

with MEMCl or BnBr (Bn=benzyl) to obtain a protected 3,5-dihalosalicylaldehyde of the formula

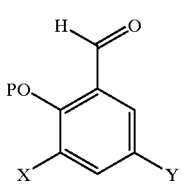

wherein P is Bn or MEM; treating the protected 3,5-dihalosalicylaldehyde with (R) or (S) phenylglycinol in tetrahydrofuran (THF) or toluene to produce an iminoalcohol of the formula

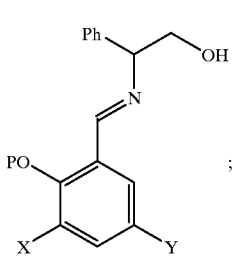

reacting said imino alcohol with BrZnCH₂CO₂-t-Bu in N-methylpyrrolidinone (NMP), dimethylsulfoxide (DMSO) or THF to produce an amino alcohol of the formula

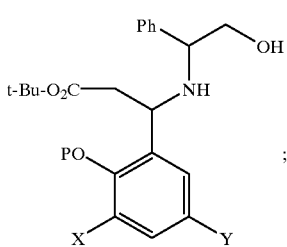

reacting the amino alcohol with lead tetracetate (Pb(OAc)₄) to form an imine of the formula

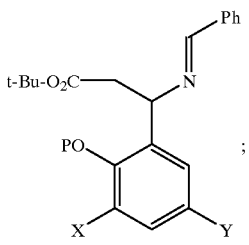

transesterifying, deprotecting, and hydrolyzing said imine in a one pot process to isolate a product of the formula

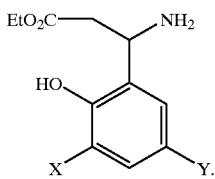

The reaction provides for the preparation of (R) or (S) isomers with enantiomeric excess (ee)>99%.

DETAILED DESCRIPTION OF THE INVENTION

The invention herein is directed to the preparation of β-amino acids and esters of the formula

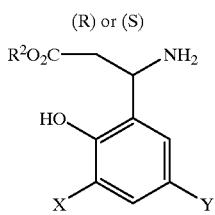

and acid addition salts thereof wherein $R^2$ is H or lower alkyl and X and Y are the same or different halo groups.

Synthetic schemes for the most preferred synthetic methods are outlined in Schemes I–IV and the following descriptions thereof.

SCHEME 1

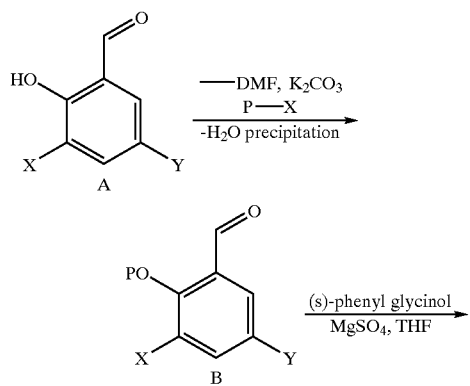

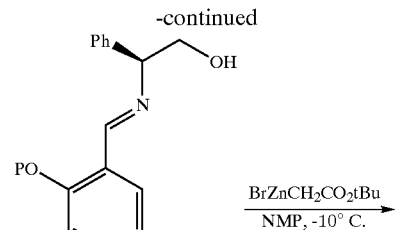

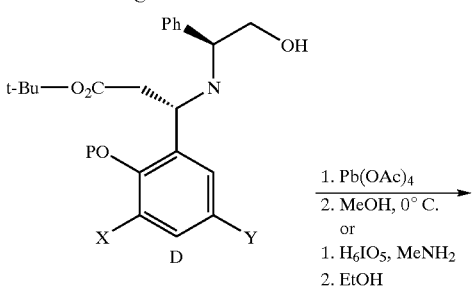

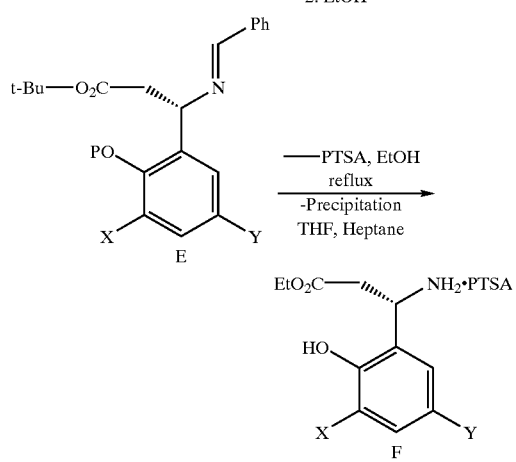

MEM: methoxyethoxymethyl
Bn: benzyl
PX = MEMCl or BnBr
P = MEM, Bn
X = Cl, Br, I
Y = Cl, Br, I In Scheme I, 3,5-dihalosalicylaldehyde (A, X, Y=Cl, Br, I) was protected as a MEM derivative (B, P=MEM, X, Y=Cl, Br, I) or benzyl derivative (B, P=Bn, X, Y=Cl) by reaction, respectively, with MEMCl or benzyl bromine and potassium carbonate in DMF. The chiral imine C was formed from B and (S)-phenyl glycinol in THF in the presence of magnesium sulfate. C was reacted with two equivalents of Reformatsky reagent ($BrZnCH_2CO_2tBu.THF$) to stereoselectively form D (P=MEM, Bn, X, Y=Cl, Br, I). The amino alcohol residue of D (P=MEM, X, Y=Cl, Br, I) was oxidatively cleaved using lead acetate in methanol to form the imines E (P=MEM, X, Y=Cl, Br, I). Alternatively the oxidative cleavage can be performed with periodic acid in ethanol in the presence of methyl amine. The β-amino esters were then prepared refluxing E (P=MEM, X, Y=Cl, Br, I) in the presence of excess of p-toluenesulfonic acid in ethanol followed by precipitation in THF/heptane. F (X, Y=Cl, Br, I) was obtained with good overall yield and high optical purity and chemical purity. Intermediates C, D, E are not isolated and are used subsequently as prepared without purification.

SCHEME II

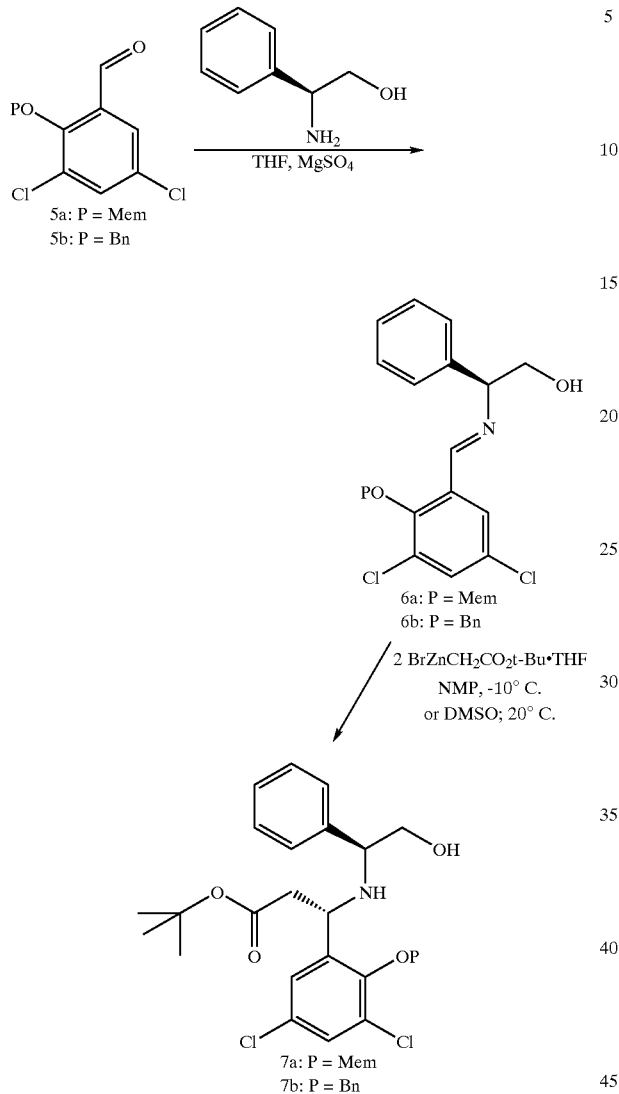

In Scheme II, the chiral imines 6a (P=MEM) and 6b (P=Bn), were prepared by reaction of the corresponding protected 3,5-dichlorosalicylaldehyde 5a (P=MEM), 5b (P=Bn) with (S)-phenyl glycinol in THF in the presence of magnesium sulfate followed by filtration and distillation of the solvent. Imine 6a was reacted with 2 equivalents of Reformatsky reagent (BrZnCH$_2$CO$_2$tBu.THF) in NMP for 1 hour at −10° C. followed by quench with HCl/NH$_4$Cl, extraction with MTBE and distillation of the solvents to obtain a crude product (100%) containing 7a as one diastereoisomer as determined by $^1$H NMR and TLC. The same reaction performed in DMSO at 20° C. led to lower selectivity as 7a is isolated as a 95/5 mixture of diastereoisomer with 86% yield after chromatography. Reaction of imine 6b (P=Bn) in NMP was slower and was completed after 15 hours at −5° C. Compound 7b was isolated as one diastereoisomer as determined by $^1$H NMR and TLC.

SCHEME III

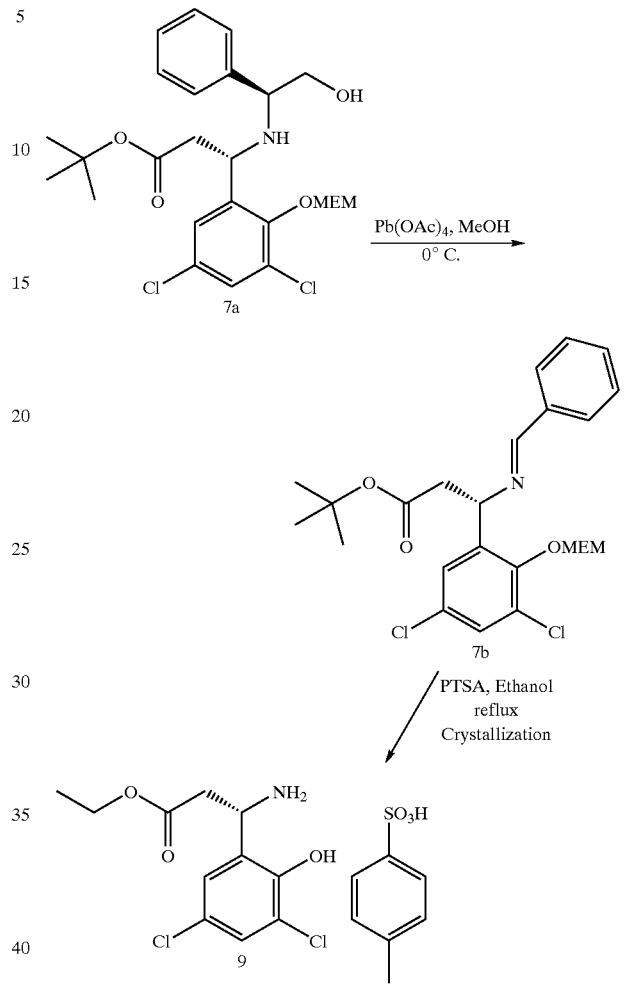

In Scheme III, the amino alcohol residue of 7a was oxidatively cleaved using lead tetra acetate in methanol to form the imine 8. 8 is refluxed in the presence of excess of p-toluenesulfonic acid in ethanol followed by precipitation in THF/heptane. The β-amino ester 9 was obtained with 49% overall yield and ee>99% as determined by chiral LC. Alternatively, the oxidative cleavage was performed with sodium periodate in ethanol in the presence of methyl amine or periodic acid in ethanol in the presence of methyl amine.

SCHEME IV

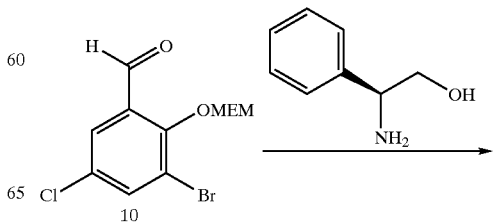

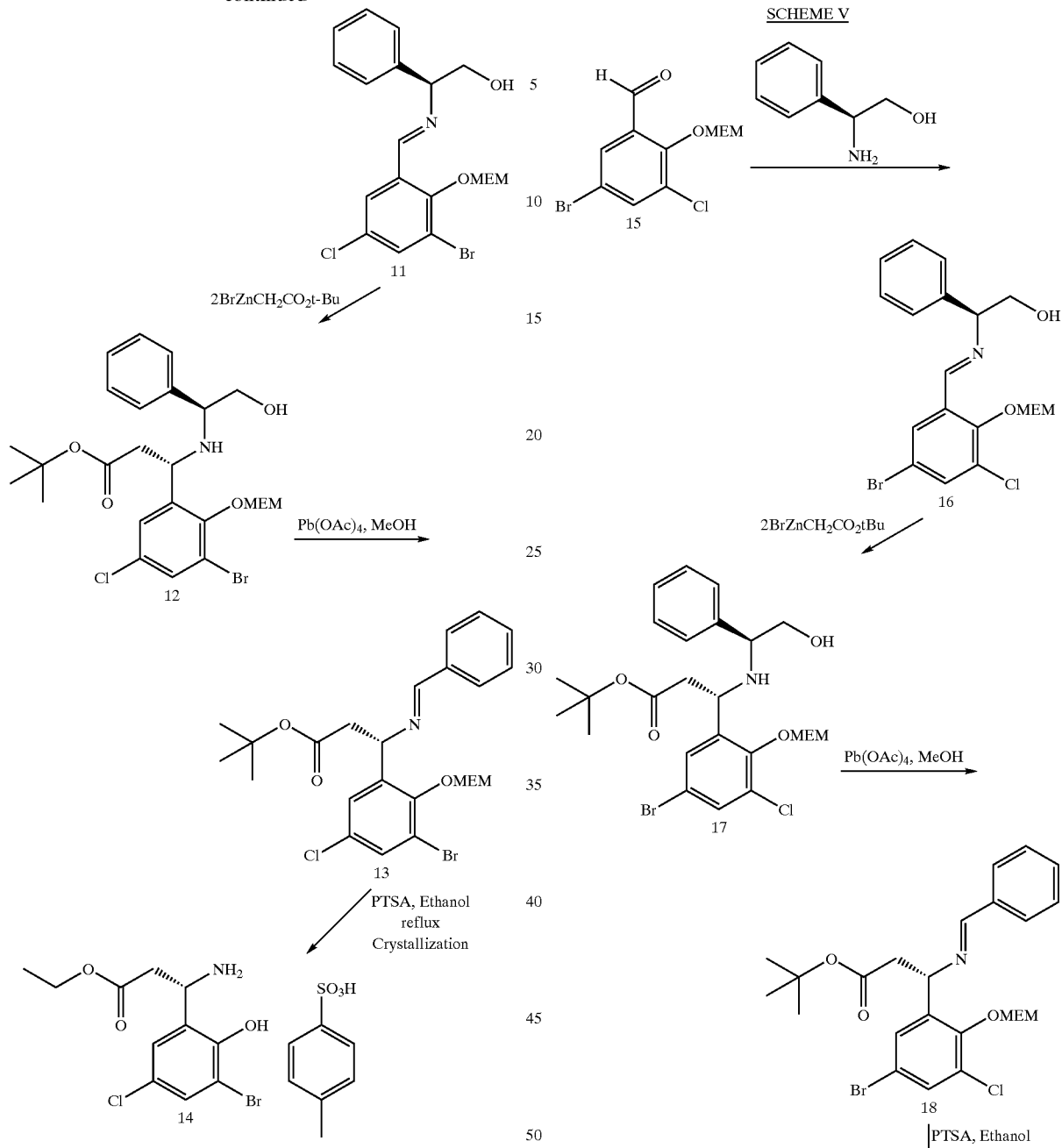

In Scheme IV, the chiral imine 11 was prepared by reaction of the corresponding protected 3-bromo-5-chlorosalicylaldehyde 10 with (S)-phenyl glycinol in THF in the presence of magnesium sulfate followed by filtration and distillation of the solvent. Imine 11 was reacted with 2 equivalents of Reformatsky reagent in NMP at −10° C. followed by quench with HCl/NH$_4$Cl, extraction with MTBE and distillation of the solvents to obtain a crude product (100%) containing 12 as one diastereoisomer (as determined $^1$H NMR). The amino alcohol residue of 12 was oxidatively cleaved using lead acetate in methanol to form the imine 13. 13 was refluxed in the presence of excess of p-toluenesulfonic acid in ethanol followed by precipitation in TF/heptane. The β-amino ester 14 was obtained with 45% overall yield (from unprotected salicylaldehyde) and ee>99% as determined by chiral LC.

In Scheme V, the chiral imine 16 was prepared by reaction of the corresponding protected 3-chloro-5-bromo salicylaldehyde 15 with (S)-phenyl glycinol in THF in the presence of magnesium sulfate followed by filtration and distillation of the solvent. Imine 16 was reacted with 2 equivalents of Reformatsky reagent in NMP at −10° C., followed by quench with HCl/NH₄Cl, extraction with MTBE, and distillation of the solvents to obtain a crude product (100%) containing 17 as one diastereoisomer as determined by ¹H NMR. The amino alcohol residue of 17 was oxidatively cleaved using lead acetate in methanol to form the imine 18. 18 was refluxed in the presence of excess of p-toluenesulfonic acid in ethanol followed by precipitation in THF/heptane. The β-amino ester 19 was obtained with 33% overall yield (from unprotected salicylaldehyde) and ee>99% as determined by chiral LC.

Unless otherwise noted the starting materials for the process of this invention are all commercially available or can be prepared according to conventional methods known to those with skill in the art. All equipment employed is commercially available.

The following is a list of definitions and abbreviations used herein:

The terms "alkyl" or "lower alkyl" refer to straight chain or branched chain hydrocarbon radicals having from about 1 to about 6 carbon atoms. Examples of such alkyl radicals include methyl, ethyl, n-propyl, isopropyl, n-butyl, isobutyl, sec-butyl, t-butyl, pentyl, hexyl and the like.

The term "L-phenylglycinol" refers to a radical of the formula

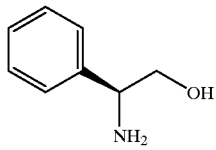

and is used interchangeably with the term (S)-phenylglycinol.

The term "D-phenylglycinol" refers to a radical of the formula

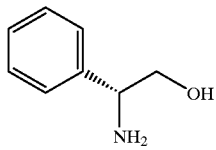

and is used interchangeably with the term (R)-phenylglycinol.

The term "halo" as used herein refers to a bromo, chloro or iodo radical.

| Ph = | phenyl |
| DI = | deionized water |
| MEMCI = | methoxyethoxymethylchloride |
| g = | grams |
| L = | liter |
| ml = | milliliter | ee means enantiomeric excess
Bn refers to a benzyl radical
MEM refers to a methoxyethoxymethyl radical
THF refers to tetrahydrofuran
NMP refers to N-methylpyrrolidinone
DMSO refers to dimethylsulfoxide
NaIO₄ refers to sodium periodate
NH₄Cl refers to ammonium chloride
CH₃NH₂ refers to methylamine
EtOH refers to ethanol
Pb(OAc)₄ refers to lead tetraacetate
PTSA refers to para-toluenesulfonic acid
MTBE refers to methyl tert-butyl ether
NaOEt refers to sodium ethoxide
EtOAc refers to ethyl acetate
MgSO₄ refers to magnesium sulfate
GC refers to gas chromatography.

The present invention provides a safe, convenient and cost effective manufacturing process for the preparation of chiral β-amino acids and esters which is amenable to scale-up. The process utilizes raw materials which are readily available and cost efficient. Its convenience is demonstrated in that the synthetic route does not require either a chromatography or chemical or enzymatic separation of diastereoisomers. Its cost effectiveness is demonstrated by the final products being produced in high yield and a high level of optical purity.

The following non-limiting examples describe and illustrate a method for carrying out the process of the present invention, as well as other aspects of the invention, and the results achieved thereby in further detail. Both an explanation of, and the actual procedures for, the various aspects of the present invention are described where appropriate. These examples are intended to be illustrative of the present invention, and not limiting thereof in either scope or spirit. Those of skill in the art will readily understand that known variations of the conditions and processes described in these examples can be used to perform the process of the present invention.

EXAMPLE 1

Preparation of

Br—ZnCH₂CO₂-t-Bu•THF

Step A

A 4 liter jacketed flask, fitted with a condenser, temperature probe, mechanical stirrer, was charged with 180 g of Zn metal (−30–100 mesh, 180.0 g, 2.76 moles) and 1.25 L of THF to the vessel. While stirring, 1,2-dibromoethane (4.74 ml, 0.05 mole) was added to the vessel via a syringe at once. After purging three times (N₂/vacuum), the suspension of zinc in THF was heated to reflux (65° C.) and maintained at this temperature for 1 hour. The mixture was cooled to 50° C. before charging the tert-butyl bromoacetate (488 g, 369 ml, 2.5 mmole) over a 1.5 hour time period. Controlled reagent addition was done by 50 ml syringe and syringe pump (addition rate set at 4.1 ml/minutes). A temperature of 50° C.+/−5° C. was maintained during the addition. The reaction mixture was allowed to stir at 50° C. for 1 hour after the addition was complete. The reaction mixture was then allowed to cool to 25° C., and upon reaching this temperature the agitation was turned off to allow the precipitated product to settle (the product precipitated from THF solution at 31° C.). The THF mother liquor was removed by decantation into a 2 L round-bottom flask which was under partial vacuum (20 mm Hg) with a dip tube ( coarse fritted glass filter). This procedure removed 65% of THF from the vessel. 800 ml of NMP is added and agitation is resumed for 5 minutes at 25° C. The reaction mixture was transferred to another vessel by filtration to remove the remaining zinc. Analytical determination of the titer was 1.57 Molar with a molar yield of 94%, following the titration method.

Note: The solid reagent can be filtered and dried under N₂ using a pressure funnel. The cake was washed with THF until obtaining a white solid. The solid was dried for 1–2 hours. Typical recovery is 85–90%. The solid can be stored at −20° C. for at least 6 months.

Step B—Titration Method

A 1.0 ml aliquot of the Reformatsky-NMP/THF solution was removed from the reaction mixture via syringe and added to a 25 ml round-bottom flask which contained a pre-weighed amount of benzaldehyde (250–300 mg) and a magnetic stir bar, under a nitrogen atmosphere. The reaction mixture was stirred for 30 minutes at room temperature. To the flask was added 5.0 ml of aqueous 29% $NH_4Cl$ and 5.0 ml of MTBE. The resulting mixture was stirred for 5 minutes at room temperature. The agitation was stopped and the layers allowed to separate over 5 minutes. A 1.0 ml aliquot of the organic layer was removed and diluted to 25 ml with MTBE in a volumetric flask. This solution was subjected to GC analysis using an HP-1 10 m column. Standard solutions of benzaldehyde in MTBE at concentrations of 0.04 M, 0.01 M, and 0.002 M were co-injected with the sample. The sample concentration was determined from the linearity plot of the standard solutions and the sample GC peak area. The concentration of the Reformatsky solution was then determined by using the following calculation:

Amount of remaining benzaldehyde concentration of sample (g/L)*50*5/2 Titer (Mole/L)=Pre-weighed amount of benzaldehyde—amount remaining/106 Yield=Mole/liter *Total volume of solution/Theoretical 100% yield

EXAMPLE 1

Preparation of

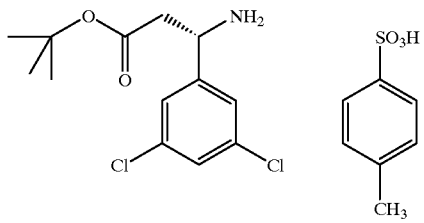

Step A
Formation of the Imine

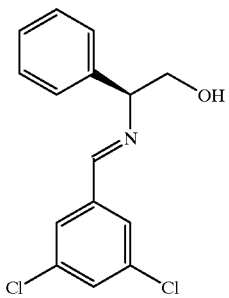

(S)-Phenyl glycinol (11.74 g, 0.086 Mole) was charged in a 500 ml 3N round-bottom flask fitted with a mechanical stirrer, followed by toluene (110 ml) and the flask was vacuum/flushed with nitrogen. 3,5-dichlorobenzaldehyde was then added at once. After 15 minutes at 22° C., $MgSO_4$ (15 g) was added. The mixture was stirred for 1 hour at 22° C., and filtered on a coarse fritted filter. The cake was washed with toluene (20 ml). The solutions were combined and concentrated under reduced pressure to afford 27.00 g of a pale yellow oil containing the imine. No further purification was performed and the crude product was used directly in the coupling reaction. $^1H$ NMR ($CDCl_3$, TMS) mixture of imine and oxazoline 4/1. (ppm):(imine) 3.88 to 3.99 (m, 2H), 4.50 (dd, 1H, J=4.7, 8.1 Hz), 7.67 (d, 2H), 8.28 (s, 1H): oxazoline: 5.55 and 5.70 (s, 0.5+0.5H), 3.72 to 3.83 (m, 0.5+0.5H), 4.30 to 4.35 (m, 0.5+0.5H), 4.40 to 4.48 (m, 0.5H), 4.54 to 4.60 (m, 0.5H), mixed protons: 7.15 to 7.47 (m(aromatic+$CDCl_3$)); $^{13}C$ NMR ($CDCl_3$, TMS) (ppm) :imine: 67.55, 76.38, 135.13, 138.70, 140.05, 159.72. Oxazoline:60.60, 62.80, 72.12, 72.34, 91.05, 91.68, 135.03, 135.41, 142.62. Mixed signals: (aromatics) 124.86, 124.956, 125.33, 126.53, 126.65, 126.75, 127.38, 127.74, 127.77, 128.11, 128.26, 128.32, 128.72, 128.84, 128.93, 129.06, 130.64.

Step B
Reformatsky Coupling

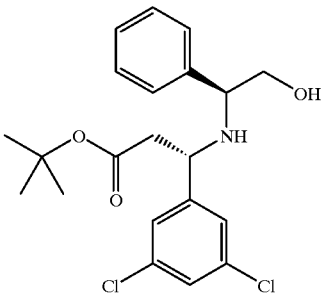

A 1 L jacketed 3 ports reactor with bottom valve, fitted with a mechanical stirrer and an addition funnel was charged with a solution of Reformatsky reagent from Example 1. The solution was then cooled to −10° C. A solution of imine in NMP (60 ml) was prepared under nitrogen and charged in the addition funnel. The solution of imine from Step A was then added over 5 minutes while the temperature was maintained at −5° C. (jacket at −10° C.). The reaction was monitored by GC and TLC (elution heptane/EtOAc 30%). After 5 minutes the reaction was almost complete (trace of starting material). The mixture was stirred for an additional hour and a mixture of 2N HCl/saturated solution of $NH_4Cl$ (1/2, 135 ml) was added. MTBE (200 ml) was added and the mixture was stirred for 1 hour at 23° C. Stirring was stopped and the layers were separated. The aqueous layer was extracted with MTBE (100 ml). The two organic layers were combined, washed successively with a saturated solution of $NH_4Cl$ (140 ml), water (140 ml) and brine (140 ml). The solution was dried with $MgSO_4$ (30 g), filtered and concentrated to afford 35.2 g of an orange oil containing the desired product as a single diastereoisomer (by $^1H$ NMR).

In a separate reaction (28.6 mmole scale) the crude product (11.36 g) was purified by chromatography [($SiO_2$, 200 g), elution heptane/EtOAc 30%] to afford the desired compound as a pale yellow oil (10.07 g, 85%). $^1H$ NMR ($CDCl_3$,TMS) (ppm)1.40 (s, 9H), 2.56 (dd (AB), 1H, J=5.6, 15.4 Hz), 2.56 (dd (AB), 1H, J=8.1, 15.6 Hz), 2.60 (s(broad), 1H), 3.62 (dd (AB), 1H, J=6.8, 10.7 Hz), 3.72 (dd, 1H, J=4.2, 6.8 Hz), 3.80 (dd (AB), 1H, J=4.2, 6.8 Hz), 4.11 (dd, 1H, J=5.8, 7.9 Hz), 7.09 to 7.29 (m, 8H, (aromatic)); $^{13}C$ NMR ($CDCl_3$, TMS) (ppm): 28.00, 42.98, 57.28, 62.24, 65.99, 81.42, 125.69, 127.21, 127.35, 127.60, 128.48, 134.83, 140.78, 146.44, 170.58; DSC: 241.46° C. (endo. 180.1 J/g); $[\alpha]^D 25=+6.9°$ (c=1.025, $CHCl_3$); IRV (MIR) (cm−1) 1726, 1587, 1567. Microanalytical: calcd for $C_{21}H_{25}Cl_2NO_3$: C, 61.47%; H, 6.14%; N, 3.41%; Cl, 17.27; found: C, 59.53%; H, 6.01%; N, 3.05%; Cl, 16.79.

Step C
Oxidative Cleavage and Salt Formation

A solution of crude ester obtained in Step B in EtOH 2B (140 ml) was charged to a 500 ml round-bottom, 3N flask. A solution of methyl amine (8.9 ml, 0.1 mole) was added. A slurry of NaIO$_4$ (0.112 mole, 25.92 g) in H$_2$O (72 ml) at 25° C. was added by portion while maintaining a temperature of 30° C. (+/−2° C.). The reaction was monitored by TLC. The reaction mixture was then stirred at room temperature for 15 hours, NaIO$_4$ (6 g, 0.026 mole) solid was added. After 4 hours, NaIO$_4$ (6 g, 0.026 mole) solid was added and the mixture was heated at 30° C. for 0.5 hour. After cooling to 25° C., the reaction mixture was concentrated under reduced pressure (water aspirator). MTBE was added and the mixture was filtered through a coarse glass fritt filter. The layers were separated and the organic layer was washed with H$_2$O (100 ml, dried with MgSO$_4$ (25 g), filtered and concentrated under reduced pressure to afford 30.2 g of an orange oil.

The crude mixture was diluted with THF (65 ml) and was charged in a 500 ml round-bottom, 3N flask fitted with a mechanical stirrer and an addition funnel. A solution of p-toluenesulfonic acid monohydrate in THF (20 ml) was then added in 2 minutes followed by a wash of THF (5 ml) via the addition funnel. After 5 minutes, heptane (65 ml) was added at once and heavy precipitation occurred. Heptane (65 ml) was added again. After 0.5 hour, the slurry was filtered through a coarse glass fritt pressure filter and was washed with heptane/THF 20% (100 ml) and heptane/THF 33% (150 ml). The cake was then dried under vacuum/nitrogen for 2 hours. The ivory solid was collected to afford the desired product (25.1 g). $^1$H NMR (CDCl$_3$, TMS) (ppm) 1.26 (s, 9H), 3.37 (s, 3H), 2.84 (dd, (AB), J=9.5, 16.3 Hz), 2.98 (dd,(AB), J=5.2, 16.2 Hz), 4.53 (m, 1H), 7.14 (d, 2H, J=7.9 Hz), 7.19 (t, 1H, J=1.8 Hz), 7.32 (d, 2H, J=8.1 Hz), 7.56 (d, 2H, J=8.1 Hz), 8.43 (s(broad), 3H); $^{13}$C NMR (CDCl$_3$, TMS) (ppm): 21.37, 27.80, 39.47, 51.36, 81.85, 125.77, 126.43, 129.01, 129.06, 135.17, 139.14, 140.59, 140.69, 168.06. DSC:120.30° C. (80.71 J/Kg), 242.63° C. (endothermic, 100.3 J/g) [α]$^P_{25}$=+37.4° (c=0.147, CHCl$_3$); IR$^v$ (MIR) (cm−1) 1726, 1587, 1567.

Microanalytical: found for C$_{20}$H$_{25}$Cl$_2$NO$_2$S: C, 51.95%; H, 5.45%; N, 3.03%; Cl, 15.33%; S, 7.02%. found: C, 51.65%; H, 5.64%; N, 3.01%; Cl, 15.13%; S, 7.00%.

EXAMPLE 3

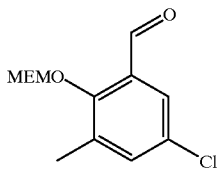

Protection of 3,5-Dichlorosalicylaldehyde

Potassium carbonate (powder, oven dried at 100° C. under vacuum, 8.28 g, 60 mmoles) was added to a solution of 3,5-dichlorosalicylaldehyde (11.46 g, 60 mmoles) in DMF (40 ml) at room temperature to give a bright yellow slurry. MEMCl (neat, 7.64 g, 61 mmoles) was then added while maintaining the bath temperature at 20° C. The mixture was then stirred at 22° C. for 3 hours and MEMCl (0.3 g, 2.4 mmoles) was added. The mixture was stirred for another 0.5 hour and was poured into 200 mL of cold water to precipitate the product. The slurry was filtered on a pressure filter, the cake was washed with water (2×50 mL) and was dried under N$_2$/vacuum to afford the product (14.94 g, 89%) as a pale yellow solid. $^1$H NMR (CDCl$_3$, TMS) 3.37 (s, 3H), 3.54 to 3.56 ( m, 2H), 3.91 to 3.93 (m, 2H), 5.30 (s, 2H), 7.63 (d, 1H, J=2.6 Hz), 7.73 (d, 1H, J=2.6 Hz), 10.30 (s, 1H); $^{13}$C NMR (CDCl$_3$, TMS) (ppm):59.03, 70.11, 99.57,126.60, 129.57, 130.81, 132.07, 135.36, 154.66, 188.30. DSC: 31.17° C. (endo 83.12 J/g);

Microanalytical: calcd for C$_{12}$H$_{16}$Cl$_2$O$_4$: C, 47.33%; H, 4.33%; Cl, 25.40%; found: C, 47.15%; H, 4.26%; Cl, 25.16%.

EXAMPLE 4

Preparation of

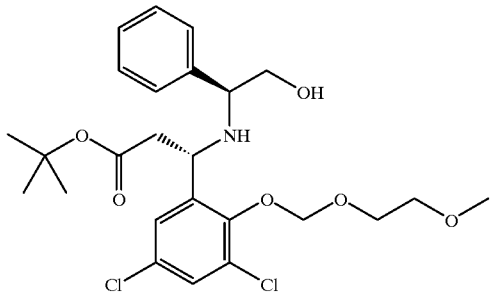

A 1 L jacketed 3 ports reactor with bottom valve, fitted with a mechanical stirrer and an addition funnel was charged with the aldehyde prepared in Example 3 (35 g, 0.125 mole) and THF (200 ml). The solution was then stirred at 22° C. and (S)-phenyl glycinol (17.20 g, 0.125 moles) was added at once. After 0.5 hour of stirring at 22° C., magnesium sulfate (15 g) was added at once. The mixture was then stirred for 1 hour at 22° C., filtered and concentrated. The residue was diluted with NMP (100 ml) and was used directly in the coupling.

A 1 L jacketed 3 ports reactor with bottom valve, fitted with a mechanical stirrer and an addition funnel was charged with solid Reformatsky reagent produced in Example 1 (91.3 g, 0.275 mole) and NMP (200 ml). The solution was then cooled to −10° C. and stirred at 350 rpm. The solution of imine in NMP was then added in 20 minutes while the temperature was maintained at −5° C. (jacket at −10° C.). The reaction was monitored by TLC (elution heptane/EtOAc 30%). After addition, the mixture was stirred 1.5 hours at −8° C. and 1 hour at −5° C. After cooling to −10° C., a mixture of concentrated HCl/saturated solution of NH$_4$Cl (8.1 mL/200 ml) was added in 10 minutes. MTBE (200 ml) was added and the mixture was stirred for 15 minutes at 23° C. at 200 rpm. Stirring was stopped and the layers were separated. The aqueous layer was extracted with MTBE (100 ml). The two organic layers were combined, washed successively with a saturated solution of NH$_4$Cl (100 ml), water (100 ml) and brine (100 ml). The solution was dried with MgSO$_4$ (30 g), filtered and concentrated to afford an orange oil (66.26 g) (solidified on standing) containing the desired product as a single diastereoisomer (confirmed by $^1$H, $^{13}$C NMR).

A sample was purified for analysis by recrystallization in heptane to afford the desired product as an off white solid. $^1$H NMR (CDCl$_3$, TMS) (ppm) 1.45 (s, 9H), 2.53 (dd, 1H, J=9.5,15.5 Hz), 2.65 (dd, 1H, J=4.4, 15.5 Hz), 3.02 (s(broad), 1H), 3.39 (s, 3H), 3.55 to 3.61 (m, 3H), 3.64 to 3.67 (m, 1H), 3.82 (d (broad), 1H, J=9.7 Hz), 3.81 to 3.98 (m, 2H), 4.61 (dd, 1H, J=4.3, 9.4 Hz), 5.14 (dd (AB syst.), 2H, J=6.2 Hz), 7.07 (d, 1H, J=2.6 Hz), 7.16 to 7.25 (m, 6H); $^{13}$C NMR (CDCl$_3$, TMS) (ppm): 27.91, 42.21, 52.46, 58.85, 62.18, 65.66, 69.47, 71.55, 81.00, 98.94, 126.51, 127.10, 127.26, 127.99, 128.16, 128.52, 129.64, 139.45, 141.28, 150.14, 170.95; DSC: 43.74° C. (endo. 54.59 J/g), 198.44° C. (endo, 97.19 J/g), 235.42° C. (endo., 59.40 J/g); $[\alpha]^D{}_{25}$=+8.7° (c=1.057, MeOH); IR (MIR) (cm$^{-1}$) 1719.

Microanalytical: calcd for $C_{25}H_{33}Cl_2NO_6$: C, 58.77%; H, 6.47%; N, 2.72%; Cl, 13.78%; found: C, 58.22%; H, 6.54%; N, 2.70%; Cl, 13.66%. Rf: 0.37 (EA 40%/Heptane 60%, UV and KMnO$_4$).

EXAMPLE 5

Preparation of

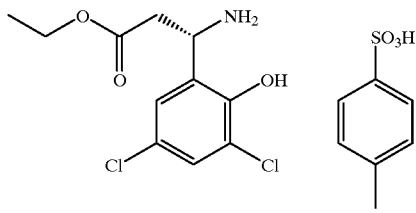

A solution of crude ester prepared in Example 4 (17.40 g, 0.033 mole (theory)) in MeOH (250 ml) was charged to a 1 L 3N jacketed reactor. The solution was cooled to 0° C. and Pb(OAc)$_4$[15 g, 0.033 mole] was added at once. After 2 hours, a 15% solution of NaOH (30 ml) was added and ethanol was removed under reduced pressure. Another 100 ml of 15% solution of NaOH was added and the mixture was extracted with MTBE (2×100 ml), washed with H$_2$O (2×100 ml) and brine (50 ml), dried with Na$_2$SO$_4$, filtered on celite and concentrated under reduced pressure to afford an orange oil (12.46 g) which was used without further purification. (Rf of intermediate 0.63) (EA 40%/heptane 60%, UV).

The oil was diluted with ethanol (30 ml) and paratoluene sulfonic acid (6.3 g, 0.033 mole) was added at once. The solution was then heated to reflux for 8 hours, cooled to room temperature and concentrated under reduced pressure. The residue was diluted with THF (20 ml) and was heated to reflux to form an homogeneous solution. The mixture was then cooled to room temperature and the compound crystallized. Heptane (30 ml) and THF (10 ml) were added to form a fluid slurry which was then filtered. The cake was washed with THF/heptane(40 ml, 1/1) and was dried for 2 hours in a pressure filter under N$_2$/vacuum to afford a white solid (7.40 g). $^1$H NMR (DMSO, TMS) (ppm) 1.12 (t, 3H, J=7.1 Hz), 2.29 (s, 3H), 2.97 (dd (AAB), 1H, J=7.4,16.5 Hz), 3.04 (dd (AB), J=7.0, 16.5 H), 4.05 (q, 2H, J=7.1 Hz), 4.88 (t, 1H, J=7.15 Hz), 7.11 (d, 2H, J=7.8 Hz), 7.44 (9d, 2H, J=2.5 Hz), 7.48 (d, 2H, J=8.1 Hz), 7.58 (2H, d, J=2.5 Hz), 8.15 (s, broad, 3H) and THF 1.76 (m, 0.25×4H), 3.60 (m, 0.25×4H); $^{13}$C NMR (CDCl$_3$, TMS) (ppm): 13.87, 21.35, 25.60, 36.28, 49.30, 61.42, 67.96, 123.52, 125.19, 125.47, 125.71, 125.84, 128.89, m 129.91, 140.57, 140.61, 149.19, 170.18 and THF 25.60, 67.96; DSC:153.23° C. (end., 61.26 J/g), 202.83° C. (exo. 21.58 J/g), 288.83° C. (133.6 J/g) $[\alpha]^D{}_{25}$=+6.7° (c=1.063, CHCl$_3$); IR (MIR) (cm-1) 3146, 2981, 2904, 1724, 1596, 1472.

Microanalytical: calcd for $C_{18}H_{21}Cl_2NO_6S$, 0.25 $C_4H_8O$: C, 48.73%; H, 4.95%; N, 2.99%; Cl, 15.14% found: C, 48.91%; H, 4.95%; N, 2.90%; Cl, 14.95%.

EXAMPLE 6

Preparation of

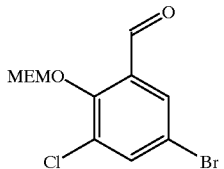

Potassium carbonate (powder, oven dried at 100° C. under vacuum), (22.1 g, 0.16 moles) was added to a solution of 3-chloro-5-bromosalicylaldehyde (35.0 g, 0.15 moles) in DMF (175 ml) at room temperature to give a bright yellow slurry. MEMCl (neat, 25.0 g, 0.2 moles) was added while maintaining the bath temperature at 20° C. The mixture was then stirred at 22° C. for 6 hours and was poured in 1200 mL of DI water to precipitate the product. The slurry was filtered on a pressure filter and the cake was washed with DI water (2×400 mL) and was dried under N$_2$/vacuum to afford the product (46.0 g, 95%) as an off white solid. $^1$H NMR (CDCl$_3$, TMS) 3.35 (s, 3H), 3.54 to 3.56 (m, 2H), 3.91 to 3.93 (m, 2H), 5.30 (s, 2H), 7.77 (d, 1H), 7.85 (d, $^1$H), 10.30 (s, 1H); $^{13}$C NMR (CDCl$_3$, TMS) (ppm):59.05, 70.11, 71.49, 99.50, 117.93, 129.69, 129.78, 132.37, 138.14, 155.12, 188.22. DSC: 48.24° C. (endo 90.51 J/g);

Microanalytical: calcd for $C_{11}H_{12}BrClO_4$: C, 40.82%; H, 3.74%; Cl, 10.95%; Br, 24.69%; found: C, 40.64%; H, 3.48%; Cl, 10.99%; Br, 24.67%.

EXAMPLE 7

Preparation of

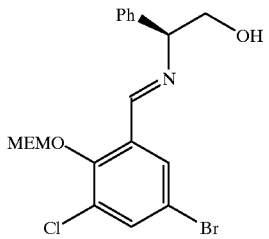

The compound prepared in Example 6 (32.35 g, 0.1 mol) was charged in a 500 ml 3N round-bottom flask fitted with a mechanical stirrer, followed by THF (160 ml) and (S)-phenylglycinol (13.71 g, 0.1 mol) was added. After 30 minutes at 22° C., MgSO$_4$ (20 g) was added. The mixture was stirred for 1 hour at 22° C. and filtered on a coarse fritted filter. The filtrate was concentrated under reduced pressure to afford a pale yellow oil (48.0 g) containing the imine. No further purification was performed and the crude product was used directly in the coupling reaction.

Microanalytical: calcd for $C_{19}H_{21}BrClNO_4$: C, 51.54%; H, 4.78%; N, 3.16%; Br, 18.04%; Cl, 8.00% found: C, 51.52%; H, 5.02%; N, 2.82%; Br, 16.31%; Cl, 7.61%.

EXAMPLE 8

Preparation of

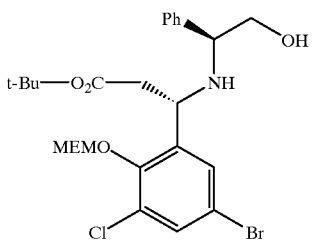

In a 5 L 3N round-bottom flask fitted with a mechanical stirrer, Reformatsky reagent from Example 1 (332.0 g, 0.8 mol) was taken up in NMP (660 mL) under nitrogen. The solution was then cooled to −10° C. A solution of imine (0.4 mol) prepared in Example 7 in NMP (320 ml) was prepared under nitrogen and then added in 30 minutes to the above reaction mixture while the temperature was maintained at −5° C. The mixture was stirred for one hour at −8° C. and at −5° C. for 2 hours and cooled to −10° C. A mixture of concentrated HCl/saturated solution of $NH_4Cl$ (30 mL/720 mL) was added in 10 minutes. The reaction mixture was stirred for 30 additional minutes. MTBE (760 ml) was added and the mixture was stirred for 1 hour at 23° C. Stirring was stopped and the layers were separated. The aqueous layer was extracted with MTBE (320 ml). The two organic layers were combined, washed successively with a saturated solution of $NH_4Cl$ (320 ml), DI water (320 ml) and brine (320 ml). The solution was dried with $MgSO_4$ (60 g), filtered and concentrated to afford a yellow oil (228 g) containing the desired product as a single diastereoisomer.

DSC; 227.54° C. (endo. 61.63 J/g);

Microanalytical calcd for $C_{25}H_{33}BrClNO_6$: C, 53.72%; H, 5.95%; N, 2.50%; Br, 14.29%; Cl, 6.33% found: C, 53.80%; H, 6.45%; N, 2.23%; Br, 12.85%; C, 6.12%.

EXAMPLE 9

Preparation of

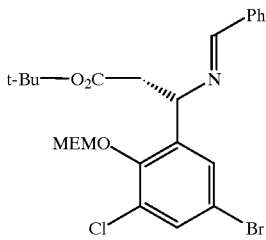

A solution of crude ester prepared in Example 8 (~111.0 g) in methanol (1500 mL) was charged under nitrogen atmosphere to a 3 L 3N round-bottom flask fitted with a mechanical stirrer. The reaction mixture was cooled to 0° C. and lead tetraacetate (88.67 g, 0.2 mol) was added in one portion. The reaction mixture was stirred for 3 hours at 0° C. and then 15% aqueous NaOH (150 mL) was added to the reaction mixture below 5° C. Methanol was removed under reduced pressure on rotavap. Another 600 mL of 15% aqueous NaOH was added and the reaction mixture was extracted with (2×300 mL) ethylacetate and (2×200 mL) MTBE and (2×200 mL) ethylacetate. Organic layers were combined and washed with (2×200 mL) DI water and (2×100 mL) brine and dried over anhydrous $MgSO_4$ (30 g). The solution was filtered over celite and concentrated under reduced pressure to give the desired product (96 g) as an orange oil.

DSC: 233.60° C. (endo. 67.85 J/g);

Microanalytical: calcd for $C_{24}H_{29}BrClNO_5$: C, 54.71%; H, 5.54%; N, 2.65%; Br, 15.16%; Cl, 6.72% found: C, 52.12%; H, 5.40%; N, 2.47%; Br, 14.77%; Cl, 6.48%.

EXAMPLE 10

Preparation of

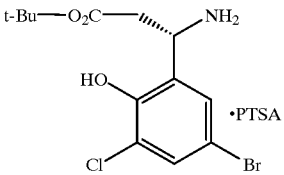

Crude product prepared in Example 9 (~94 g), was taken in absolute ethanol (180 mL) and para toluenesulfonic acid monohydrate (50.0 g, 0.26 mol) was added. The reaction mixture was then heated to reflux for 8 hours after which the solvent was removed under reduced pressure. Residual solid was taken up in THF (100 mL) and the THF was then stripped off under reduced pressure. Residue was dissolved in ethylacetate (500 mL) and cooled to ~5° C. Solid was filtered and washed with (2×50 mL) heptane to give a white solid. The solid was air dried to give the desired product (38 g) as a single isomer as a white solid. $^1$H NMR (DMSO, TMS) (ppm) 1.12 (t, 3H), 2.29 (s, 3H), 3.0 (m, 2H), 4.05 (q, 2H), 4.88 (t, 1H), 7.11 (d, 2H), 7.48 (d, 2H), 7.55 (d, 1H), 7.68 (1H, d), 8.35 (br. s, 3H); $^{13}$C NMR(DMSO,TMS) (ppm):13.82, 20.75, 37.13, 45.59, 60.59,110.63, 122.47, 125.44, 127.87, 128.06, 129.51, 131.95, 137.77, 145.33, 150.14, 168.98; DSC:69.86° C. (endo 406.5 J/g), 165.72° C. (end. 62.27 J/g), 211.24° C. (exo. 20.56 J/g) $[\alpha]^D_{25}$=+4.2° (c=0.960, MeOH); IR (MIR) (cm-1) 2922, 1726, 1621, 1591, 1494, 1471, 1413, 1376, 1324, 1286, 1237, 1207.

Microanalytical: calcd for $C_{18}H_{21}BrClNO_6S$: C, 43.69%; H, 4.27%; N, 2.83%; Br, 16.15%, Cl, 7.16%, S, 6.48%; found: C, 43.40%; H,4.24%; N, 2.73%; Br, 16.40%, Cl, 7.20%; S, 6.54%.

EXAMPLE 11

Preparation of

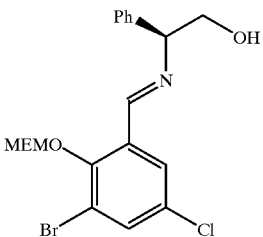

MEM protected 3-bromo-5-chlorosalicylaldehyde (129.42 g, 0.4 mol) was charged in a 2000 ml 3N round-bottom flask fitted with a mechanical stirrer, followed by addition of THF (640 ml) and (S)-phenylglycinol (54.86 g, 0.4 mol). After 30 minutes at 22° C., $MgSO_4$ (80 g) was added. The mixture was stirred for 2 hours at 22° C., and filtered on a coarse fritted filter. The filtrate was concentrated under reduced pressure to afford a pale yellow oil (180.0 g) containing the imine. No further purification was performed and the crude product was used directly in the coupling reaction.

Microanalytical: calcd for $C_{19}H_{21}BrClNO_4$: C, 51.54%; H, 4.78%; N, 3.16%; Br, 18.04%; Cl, 8.00% found: C, 50.22%; H, 4.94%; N, 2.93%; Br, 17.15%; Cl, 7.56%.

EXAMPLE 12

Preparation of

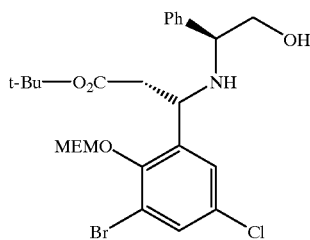

In a 5 L 3N round bottom flask fitted with a mechanical stirrer, reagent from Example 1 (332.0 g, 0.8 mol) was taken up in NMP (660 mL) under nitrogen. The solution was then cooled to −10° C. A solution of imine (180 g, 0.4 mole) prepared in Example 11 in NMP (320 ml) was prepared under nitrogen and then added in 30 minutes to the above reaction mixture while the temperature was maintained at −5° C. The mixture was stirred for an additional hour at −8° C. and at −5° C. for 2 hours after addition was complete. The mixture was cooled to −10° C. A mixture of concentrated HCl/saturated solution of $NH_4Cl$ (30 mL/720 mL) was added over 10 minutes. MTBE (760 ml) was added and the mixture was stirred for 30 minutes at 23° C. Stirring was stopped and the layers were separated. The aqueous layer was extracted with MTBE (320 ml). The two organic layers were combined, washed successively with a saturated solution of $NH_4Cl$ ( 320 ml), DI water (320 ml) and brine (320 ml). The solution was dried with $MgSO_4$ (60 g), filtered and concentrated to afford a yellow oil (221.0 g) containing the desired product as a single diastereoisomer.

DSC: 211.80° C. (endo. 72.56 J/g), 228.34° C. (98.23 J/g);

Microanalytical: calcd for $C_{21}H_{33}BrClNO_6$: C, 53.72%; H, 5.95%; N, 2.50%; Br, 14.29%; Cl, 6.33%; found: C, 52.11%; H, 6.09%; N, 2.34%; Br, 12.84%; Cl, 6.33%.

EXAMPLE 13

Preparation of

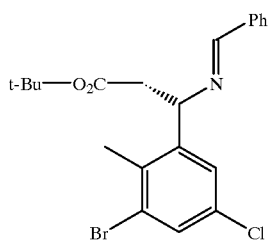

A solution of crude ester prepared in Example 12 (~111 g), in methanol (1500 mL) was charged under argon atmosphere to a 3 L 3N round-bottom flask fitted with a mechanical stirrer. The reaction mixture was cooled to 0° C. and lead tetraacetate (88.67 g, 0.2 mol) was added in one portion. The reaction mixture was stirred for 3 hours at 0° C. and then 15% aqueous NaOH (150 mL) was added to the reaction mixture below 5° C. Methanol was removed under reduced pressure on rotavap. Additional 15% aqueous NaOH (150 ml) was added and the reaction mixture was extracted with ethylacetate (3×300 mL) and washed with DI (2×100 mL ) water and brine (2×100 mL) and dried over anhydrous $MgSO_4$ (30 g). The mixture was then filtered over celite and concentrated under reduced pressure to give the desired product (103 g) as a red oil.

DSC: 197.82° C. (exo.), 204.17° C., 213.24° C. and 225.38° C. (endo.),

Microanalytical: calcd for $C_{24}H_{29}BrClNO_5$: C, 54.71%; H, 5.54%; N, 2.65%; Br, 15.16%; Cl, 6.72%; found: C, 50.13%; H, 5.21%; N, 2.39%; Br, 13.98%; Cl, 6.21%.

EXAMPLE 14

Preparation of

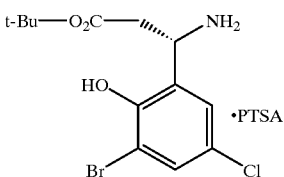

Crude product from Example 13 (~102.0 9) was taken up in absolute ethanol (180 mL) and para toluenesulfonic acid monohydrate (50 g, 0.26 mol) was added. The reaction mixture was then heated to reflux for 8 hours after which the solvent was removed under reduced pressure. Residual solid was taken up in THF (100 mL) and the THF was then stripped off under reduced pressure. The residue was dissolved in THF (200 mL) on warming to 40° C. Heptane (400 ml) was added and the reaction mixture was cooled to 30° C. A thick slurry precipitated out which was filtered with 1:1 THF/heptane solution (200 mL). The solid was washed with acetone (3×100 mL) and dried under vacuum at 40 psi under a blanket of nitrogen at 48° C.–49° C. for 16 hours to afford the desired product (55 g) as a white solid. $^1$H NMR (DMSO, TMS) (ppm) 1.14 (t, 3H), 2.29 (s, 3H), 3.0 (m, 2H), 4.05 (q, 2H),4.9 (t, 1H), 7.11 (d, 2H), 7.48 (dd, 3H), 7.70 (d, 1H), 8.35 (br. s, 3H); $^{13}$C NMR (DMSO, TMS) (ppm): 13.82, 20.76, 37.20, 45.76, 60.60, 112.47, 124.08, 125.45, 127.21, 127.63, 128.10, 132.19, 137.88, 145.19, 150.73, 168.98; DSC: 146.19° C. (endo.), 178.15° C. (end., 68.66 J/g), 210.63° C. (exo.); $[\alpha]^D_{25}$=+6.30 (c=1.110, MeOH); IR (MIR) (cm−1) 3036, 2980, 2903, 2857, 1722, 1595, 1486, 1467, 1419, 1376.

Microanalytical: calcd for $C_{18}H_{21}BrClNO_6S$, C, 43.69%; H, 4.27%; N, 2.83%; Br, 16.15%; Cl, 7.16%; S, 6.48%; found: C, 44.47%; H, 4.46%; N, 2.66%; Br, 15.15%; Cl, 7.05%; S, 6.52%.

EXAMPLE 15

Preparation of

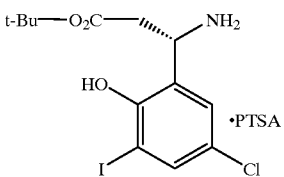

The above compound was prepared using procedures analogous to those described herein substituting the appropriate starting materials.

EXAMPLE 16
Preparation of

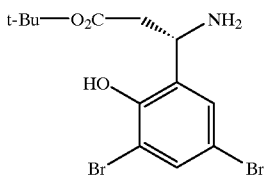

The above compound was prepared using procedures analogous to those described herein substituting the appropriate starting materials.

EXAMPLE 17
Preparation of 2-O-(MEM)-3,5-diiodosalicylaldehyde

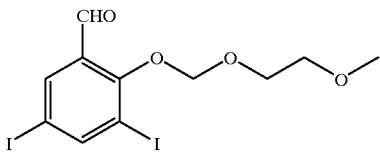

Potassium carbonate (18.5 g, 0.134 mole) was added to a solution of 3,5-diiodosalicylaldehyde (50.0 g, 0.134 mole) in DMF (150 mL) at 20° C. This resulted in a yellow slurry and MEM-Cl (15.8 mL, 0.134 mole) was added maintaining the reaction temperature. After 2 hours, additional MEM-Cl (1.5 g) was added. After stirring for a further 1 hour, the reaction mixture was poured into ice-water and stirred. The precipitate formed, was filtered, and dried in vacuo to afford the desired protected aldehyde (61 g, 99% yield). $^1$H NMR was consistent with the desired product.

EXAMPLE 18
Preparation of

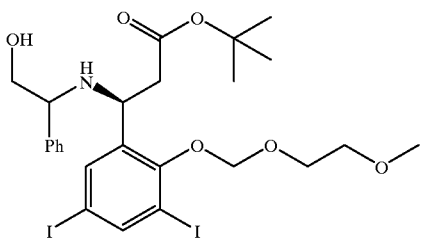

(S)-phenyl glycinol (17.9 g, 0.13 mole) was added to a solution of 2-O-(MEM)-3,5-diiodosalicylaldehyde (41.5 g, 0.112 mole) in THF (150 mL) at room temperature. After 1 hour of stirring MgSO$_4$ (20.7 g) was added and the stirring was continued for 2 hours. The reaction mixture was filtered and the filtrate was concentrated and dried in vacuo for 2 hours. A 2-neck round bottomed flask was charged with the Reformatsky reagent (96 g, 0.289 mole) and N-methylpyrrolidone (250 mL) and was stirred at –10° C. A solution of the imine in N-methylpyrrolidone (100 mL) was slowly added maintaining the temperature at –10° C. The mixture was maintained at this temperature for 2 hours and for 1 hour at –5° C. After cooling the reaction mixture to –10° C., a solution of concentrated HCl in saturated ammonium chloride (16 ml/200 mL) was added. Ethyl ether (500 mL) was added and the mixture was stirred for 2 hours at room temperature. The ether layer was separated, and the aqueous layer further extracted with ether (300 mL). The combined ether layers was washed with saturated ammonium chloride (200 mL), water (200 mL), brine (200 mL), dried (MgSO$_4$) and concentrated to afford an oil (90.0 g, 99% yield). NMR indicated desired product and one diastereomer.

EXAMPLE 19
Preparation of

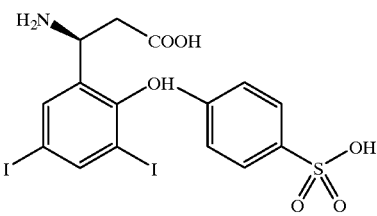

A solution of the crude ester from Example 18 (14.0 g, 20.1 mmol) was dissolved in ethanol (100 mL) and was cooled to 0° C. Lead tetra acetate (9.20 g, 20.75 mmol) was added in one lot. After 3 hours, 15% solution of NaOH (73 mL) was added to the reaction mixture. Most of the ethanol was removed under reduced pressure. The residue was added to a 15% solution of NaOH (200 mL) which was extracted with ether (400 mL). The ether layer was washed with water (100 mL), brine (100 mL), dried and concentrated to afford an orange oil. This was dissolved in ethanol (100 mL) and para-toluenesulfonic acid (6.08 g) was added. The solution was heated at reflux for 8 hours and was concentrated under reduced pressure. The residue was diluted with THF (60 mL), was heated at reflux and was cooled. Upon storage, no precipitate formed. The reaction mixture was concentrated and purified by preparative hplc to afford the amino acid as its PTSA salt. The solid obtained was dissolved in ethanol and was saturated with HCl gas. The reaction mixture was heated at reflux for 6 hours. The reaction mixture was concentrated to afford the PTSA salt of the desired amino acid (12.47 g) as its ethyl ester.

What is claimed is:

1. A process for the preparation of chiral β-amino acids of the formula

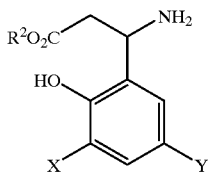

wherein X and Y are the same or different halo group; wherein $R^2$ is H or lower alkyl which process comprises reacting a 3,5-dihalosalicylaldehyde of the formula

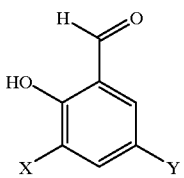

with MEMCl to produce a protected 3,5 dihalosalicylaldehyde of the formula

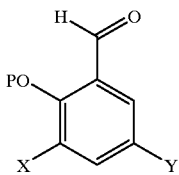

where P is MEM;

treating the protected 3,5-dihalosalicylaldehyde with (R) or (S) phenylglycinol in THF or toluene to produce an imino alcohol of the formula

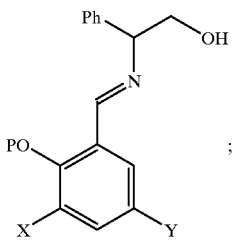

reacting said imino alcohol with BrZnCH$_2$CO$_2$-t-Bu in NMP, DMSO or THF to produce an amino alcohol of the formula

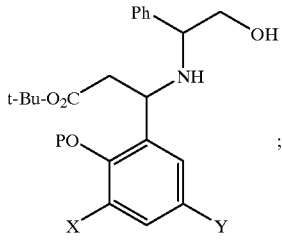

reacting the amino alcohol with lead tetraacetate, sodium periodate or periodic acid to produce an imine of the formula

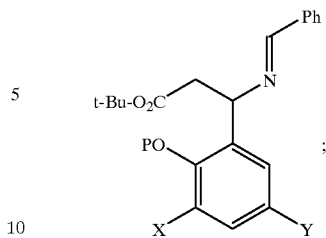

transesterifying, deprotecting and hydrolyzing said imine and isolating a chiral product of the formula

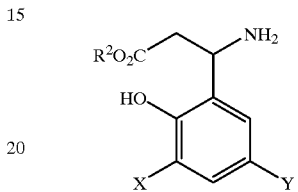

or an acid addition salt thereof.

2. The process according to claim 1 wherein X is Cl and Y is Cl.

3. The process according to claim 1 wherein X is Cl and Y is Br.

4. The process according to claim 1 wherein X is Br and Y is Cl.

5. The process according to claim 1 wherein X is I and Y is Cl.

6. The process according to claim 1 wherein X is Br and Y is Br.

7. The process according to claim 1 wherein X is I and Y is I.

8. The process according to claim 1 wherein X is Cl and Y is I.

9. The process according to claim 1 wherein X is Br and Y is I.

10. The process according to claim 1 wherein X is I and Y is Br.

* * * * *